(12) United States Patent
Hoegele (10) Patent No.: US 8,353,596 B2
(45) Date of Patent: Jan. 15, 2013

(54) ILLUMINATION DEVICE AS WELL AS OBSERVATION DEVICE

(75) Inventor: Artur Hoegele, Oberkochen (DE)

(73) Assignee: Carl Zeiss Meditech AG, Jena (DE)

(*) Notice: Subject to any disclaimer, the term of this patent is extended or adjusted under 35 U.S.C. 154(b) by 75 days.

(21) Appl. No.: 12/653,973

(22) Filed: Dec. 18, 2009

(65) Prior Publication Data

US 2010/0321637 A1    Dec. 23, 2010

(30) Foreign Application Priority Data

Dec. 18, 2008    (DE) .......................... 10 2008 062 352

(51) Int. Cl.
*A61B 3/10* (2006.01)
*A61B 3/00* (2006.01)
*G02B 21/08* (2006.01)

(52) U.S. Cl. ........ 351/221; 351/200; 351/205; 359/385; 359/388

(58) Field of Classification Search .................. 351/221, 351/200, 205, 210, 222–223, 206, 208, 211, 351/214, 213; 359/802, 798, 803, 808, 816, 359/362, 375, 399, 404, 409, 431, 629, 640, 359/368, 381, 618, 625, 636–639, 372, 389

See application file for complete search history.

(56) References Cited

U.S. PATENT DOCUMENTS 5,072,731 A    12/1991    Taratuta et al.

(Continued)

FOREIGN PATENT DOCUMENTS

| DE | 2 021 784 A1 | 11/1970 |
|---|---|---|
| DE | 43 44 770 A1 | 6/1995 |
| DE | 198 24 460 A1 | 12/1999 |

(Continued)

OTHER PUBLICATIONS

Harry Paul, Ed.: "Lexikon der Optik, Bd M bis Z" 2003, Springer Akademischer Verlag GmbH, Heidelberg, XP002439491.

*Primary Examiner* — Dawayne A Pinkney
(74) *Attorney, Agent, or Firm* — Kriegsman & Kriegsman (57) ABSTRACT

Among other items, an illumination device (110) is [provided] for an observation device (100) having one, two or more observation beam paths, each with at least one observation beam bundle, in particular for an operating microscope, having at least one light source (112) for producing at least one illumination beam path with at least one illumination beam bundle (121, 122, 123) for illuminating an object to be observed, in particular, an eye to be observed, in addition having at least one illumination optics unit (11)*, which is constructed according to the Köhler principle of illumination, as well as an objective element (119), wherein the at least one illumination beam path or the at least one illumination beam bundle (121, 122, 123) runs coaxially to an observation beam path or observation beam bundle. In order to produce an optimal solution to the problem of practical requirements relative to homogeneity of the red reflex with a simultaneous good contrasting of the lens pieces or membranes in the lens capsule, it is provided that an intermediate image (125) of the light source (112) lies in the front focal point of the objective element (119), viewed in the direction of the light, or that an intermediate image (125a) of the light source (112) lies at a distance from the front focal point of the objective element (119) corresponding to a maximum of 50% of the focal length of the objective element (119), viewed in the direction of the light.

*sic: (111)?—Trans. Note.

15 Claims, 4 Drawing Sheets

U.S. PATENT DOCUMENTS

| | | | |
|---|---|---|---|
| 5,867,251 A | 2/1999 | Webb | |
| 6,003,993 A | 12/1999 | Webb | |
| 2004/0057108 A1 | 3/2004 | Namii | |
| 2005/0128574 A1* | 6/2005 | Reimer et al. | 359/389 |
| 2007/0268575 A1* | 11/2007 | Yamazaki | 359/389 |
| 2009/0213329 A1* | 8/2009 | Kandel et al. | 351/206 |
| 2010/0309433 A1 | 12/2010 | Merz et al. | |

FOREIGN PATENT DOCUMENTS

| | | |
|---|---|---|
| DE | 20 2004 019 849 U1 | 3/2005 |
| DE | 103 47 732 A1 | 5/2005 |
| DE | 10 2004 050 651 A1 | 3/2006 |
| DE | 10 2006 013 761 A1 | 9/2007 |
| WO | WO 02/26121 A1 | 4/2002 |

* cited by examiner

FIG. 1

Optical data of the stereo coaxial illumination, designed for a principal objective with 200 mm focal length

| SURFACE | RADII | THICKNESS | GLASSES | REFRACTIVE INDEX at 546.07 nm | ½ FREE DIAMETER | COMMENTARY |
|---|---|---|---|---|---|---|
| 0 | 0.000000000 | 0.000000000 | | 1.00000000 | 0.900 | |
| 1 | 0.000000000 | 0.000000000 | | 1.00000000 | 0.900 | Light source |
| 2 | 0.000000000 | 1.000000000 | | 1.00000000 | 1.600 | |
| 3 | 0.000000000 | 9.000000000 | N-SK2 | 1.60993700 | 4.900 | |
| 4 | -8.000000000 | 0.300000000 | | 1.00000000 | 4.900 | |
| 5 | 0.000000000 | 3.000000000 | N-SK2 | 1.60993700 | 4.900 | |
| 6 | -17.200000000 | 0.300000000 | | 1.00000000 | 4.900 | |
| 7 | 17.200000000 | 3.000000000 | N-SK2 | 1.60993700 | 4.900 | |
| 8 | 0.000000000 | 4.100000000 | | 1.00000000 | | |
| 9 | 0.000000000 | 0.000000000 | | 1.00000000 | | Luminous-field diaphragm |
| 10 | 0.000000000 | 46.000000000 | | 1.00000000 | 4.100 | |
| 11 | 57.876000000 | 3.000000000 | N-LAF7 | 1.75459300 | 7.000 | |
| 12 | -44.668000000 | 1.000000000 | | 1.00000000 | 7.000 | |
| 13 | -25.119000000 | 6.000000000 | N-SF1 | 1.72307700 | 7.000 | |
| 14 | 58.715000000 | 4.882283000 | | 1.00000000 | 7.300 | |
| 15 | 0.000000000 | 10.000000000 | N-PSK53 | 1.62247100 | 8.000 | |
| 16 | -26.799000000 | 10.000000000 | | 1.00000000 | 8.700 | |
| 17 | 0.000000000 | 0.000000000 | | 1.00000000 | 8.700 | |
| 18 | 0.000000000 | 7.000000000 | | 1.00000000 | 8.700 | |
| 19 | 0.000000000 | 193.000000000 | | 1.00000000 | | Image of the light source |
| 20 | 0.000000000 | 0.000000000 | | | | Position of the principal objective |

Relay optics unit

FIG. 8

ILLUMINATION DEVICE AS WELL AS OBSERVATION DEVICE

The present invention relates first to an illumination device for an observation device according to the preamble of patent claim 1. In addition, the invention relates to an observation device according to the preamble of patent claim 11.

For example, an observation device may involve an operating microscope. In particular, the observation device can be designed as an ophthalmologic operating microscope, which is utilized, for example, for a special application in eye surgery, i.e., cataract surgery.

In the case of cataract surgery, a lens of the eye—which is clouded, for example, due to the cataract—is replaced by an artificial lens.

The lens of an eye is found inside a thin envelope, the so-called lens capsule. In order to remove the lens of the eye, access to the lens is created by a thin incision made in the lens capsule and the lens of the eye is first broken up into small pieces with a microsurgical instrument, and then these pieces are removed by means of an aspirating device.

This process takes place under microscopic observation—for example, under stereomicroscopic observation—employing a specially designed illumination device for such interventions. This illumination device presents both an illumination of the surrounding field, which is necessary for illuminating the entire operating field, as well as a red background illumination for the actual surgical field limited to the pupil region of the lens of the eye, which is of decisive importance for the cataract operation. This red background illumination is due to the fraction of illuminating light, which, passing through the transparent media of the eye, finally strikes the retina, which appears red due to good blood perfusion, is reflected therefrom, and then can also be observed, of course, as an apparent red background illumination, by the surgeon by means of the operating microscope. This very characteristic red background illumination in cataract surgery is generally known in professional circles under the term "red reflex".

For an optimal recognition of details relevant to the cataract operation, a red background illumination that is as homogeneous as possible has been proven to be a necessary prerequisite for the surgeon. A first requirement of the illumination device is thus to assure a homogeneity of the red reflex that is as optimal as possible over the entire pupil of the patient.

For complete elimination of the lens pieces of the lens of the eye that has been broken up into small pieces, and for good recognition of transparent membranes, for example, of the lens capsule, another requirement must be fulfilled, that is, a good contrasting of phase objects and, in fact, this contrast should also be provided as much as possible over the entire pupil of the patient.

For surgery on the eye, and here, in particular, in cataract operations, a homogeneous, bright "red reflex" is required along with a good contrasting of phase objects over the entire region of the pupil of the patient's eye.

The operating microscopes used in the prior art fulfill these requirements for regions of the pupil that are of varying size. A compromise must always be made between the primary requirements of a good, homogeneous "red reflex" and a good contrasting of phase objects.

For the most part, illumination is provided at a small angle for observation. This has the consequence, however, that the "red reflex" does not appear uniformly bright over the patient's pupil. An illuminating angle between 2 and 4 degrees has previously proven favorable. At this angle, one obtains a good compromise between good contrasting and illumination of the patient's pupil. Solutions in which illumination is made at an angle to the observation are described, for example, in DE 4,344,770 A1 or DE 20 2004 019 849 U1. With this arrangement, however, the "red reflex" reacts sensitively to a rolling of the patient's eye during the operation. Additional problems may occur when the patient's pupil is small or in connection with the refraction of the patient's eye. In the known solutions, the "red reflex" is not formed homogeneously.

For eye surgery, particularly in cataract surgeries, however, the surgeon requires a homogeneous, contrast-rich "red reflex".

Tests with coaxial illumination in fact led to a good, homogeneous "red reflex", but to a poor contrasting of phase objects, and thus previously have not proven useful in practice. In this case, the illuminating optics were disposed such that an illuminating mirror (or prism) lay between the two beam paths of the stereomicroscope. Therefore, this did not provide a precise 0° illumination, which is exactly produced from the same direction as the observation.

One possibility for obtaining a homogeneous, bright "red reflex" simultaneously with good contrast can be achieved by designing an illumination device having a light source with optical elements that are provided between the light source and an objective element, in such a way that the imaging of the illuminating pupil is imaged on the fundus of an eye to be observed. Such a solution is described, for example, in the older Application DE 103 47 732 A1 of the Applicant.

Another possibility for obtaining a homogeneous, bright "red reflex" simultaneously with good contrast can be achieved by providing an illumination device for an observation device having one, two or more observation beam paths, each with at least one observation beam bundle, in particular for an operating microscope, having at least one light source for producing at least one illumination beam path with at least one illumination beam bundle for illuminating an object to be observed, in particular, an eye to be observed, whereby the illumination device has at least one illumination optics unit that is constructed according to the Köhler principle of illumination, and whereby the at least one illumination beam path or the at least one illumination beam bundle runs coaxially to an observation beam path or observation beam bundle. Such a solution is described, for example, in the older Application DE 10 2006 013 761.2 A1 of the Applicant.

Starting from the named prior art, the object of the present invention is to further develop an illumination device as well as an observation device of the type named initially, in such a way that an optimal solution to the problem of practical requirements can be provided relative to homogeneity of the red reflex with a simultaneous good contrasting of the lens pieces or membranes in the lens capsule.

The problem is solved according to the invention by the illumination device with the features according to the independent patent claim 1 as well as the observation device with the features according to the independent patent claim 11. Further features and details of the invention can be taken from the subclaims, the description and the drawings. Features and details that are described in connection with the illumination device according to the invention thus obviously also apply in connection with the observation device according to the invention, and vice versa.

According to the first aspect of the invention, an illumination device is provided for an observation device having one, two or more observation beam paths, each path having at least one observation beam bundle, particularly for an operating microscope, having at least one light source for producing at least one illumination beam path having at least one illumination beam bundle for illuminating an object to be observed, in particular, an eye to be observed, in addition having at least one illumination optics unit, which is constructed according to the Köhler principle of illumination, as well as an objective element, in which the at least one illumination beam path or the at least one illumination beam bundle runs coaxially to an observation beam path or observation beam bundle. The illumination device is characterized according to the invention by the fact that an intermediate image of the light source lies in the front focal point of the objective element, viewed in the direction of the light, or that an intermediate image of the light source lies at a distance from the front focal point of the objective element corresponding to a maximum of 50% of the focal length of the objective element, viewed in the direction of the light.

The lighting device according to the invention may find application, in particular, as a two-channel stereo coaxial illumination, but of course, the invention is not limited to this, which is a special application purpose. When an illumination optics unit is used according to the Köhler principle of illumination, the light source, or an image of the light source is imaged to infinity by the objective element and after this, onto the fundus of an eye to be observed. A luminous field diaphragm of the Köhler illumination optics unit is imaged in the back focal point or in the object plane of the objective element by subsequent optical elements—viewed in the direction of the light.

In contrast to the solutions known from the prior art, it is now provided that the intermediate image of the light source is no longer found in the focal point of an optics sub-unit of the illumination optics unit, but that the intermediate image of the light source is found in the front focal point of the objective element—viewed in the direction of the light—or, however, in a certain region relative to the front focal point of the objective element. For the last-named case, this means that an intermediate image of the light source, viewed in the direction of the light, lies at a site which represents a percent deviation of plus/minus 50% of the focal length of the objective element relative to the site of the focal point of the objective element. This especially means that an intermediate image of the light source is found at a distance from the front focal point of the objective element that corresponds to the maximum 50% of the focal length of the objective element, viewed in the direction of the light. The intermediate image of the light source is imaged to infinity by the objective element. This corresponds to the imaging of the light source on the fundus of an eye to be observed.

A true coaxial illumination will be created with the present invention. "Coaxial" is therefore generally understood as an illumination near the axis. This includes both an illumination under precisely zero degree as well as an oblique illumination at a very small angle near the axis. Therefore, those solutions with slight deviations from the coaxial illumination arrangement are also included by the present invention.

According to the invention, the illumination device is provided for an observation device, but the invention is not limited to specific types of observation devices. For example, but not exclusively, the observation device can involve an operating microscope. Several non-exclusive examples for possible application purposes in the field of operating microscopes are described in detail in connection with the observation device according to the invention.

In the simplest case, a single illumination beam path with a single illumination beam bundle is provided. However, embodiments with one illumination beam path having two or more illumination beam bundles are also possible, as well as embodiments with two or more illumination beam paths, each illumination beam path in turn having at least one illumination beam bundle.

According to the invention, it is additionally provided that the illumination device has an illumination optics unit designed in a special manner. This illumination optics unit is first characterized in that it is constructed according to the Köhler principle of illumination.

The illumination optics unit constructed according to the Köhler principle first has a collector. This collector can advantageously comprise one or more individual or combined lens element(s). In addition, an aperture diaphragm is provided. This can be designed, for example, as a fixed or variable diaphragm. The light source is imaged by the collector in an intermediate image (aperture diaphragm). In addition, a condenser also is a part of the Köhler illumination. Finally, an iris diaphragm—also called a luminous field diaphragm—which can be designed advantageously as a fixed or variable diaphragm—is also part of the Köhler illumination.

Advantageously, the at least one illumination optics unit is designed in a way that the light source will be imaged on the fundus of an eye to be observed. If the object to be observed involves an eye, the cornea of the eye can be illuminated telecentrically in this way with the illumination device according to the invention. In addition, the eye further images the light source on the retina. This light is then reflected at the red retina and illuminates uniformly, intensively and in a contrast-rich manner the lens of the eye that is to be operated on.

The essence of the present invention thus first lies in a novel conception of the illumination device. The novel conception for the illumination device, among other things, consists of the fact that it produces at least one beam bundle, wherein the optical axis of this beam bundle runs coaxially to the optical axis of an observation beam bundle.

In addition, the illumination optics unit is designed in such a way that an intermediate image of the light source lies in the front focal point of the objective element, viewed in the direction of the light, or that an intermediate image of the light source lies at a distance from the front focal point of the objective element corresponding to a maximum of 50% of the focal length of the objective element, viewed in the direction of the light.

Advantageously, an aperture diaphragm can be installed at the site of the intermediate image of the light source, whereupon the cross section of the illumination beam can be precisely defined or limited.

In another embodiment, the illumination device can have at least one objective element. The objective element can also be designed as an objective element of an observation device, in particular as its principal objective. However, this is not absolutely necessary.

In another embodiment, an intermediate image of the light source can lie in front of the front focal point of the objective element or behind the front focal point of the objective element, viewed in the direction of the light. It can be provided advantageously that the intermediate image of the light source lies at a distance from the front focal point of the objective element corresponding to a maximum of 40%, preferably 30%, particularly preferred 20% of the focal length of the objective element, viewed in the direction of the light.

Deviations from the imaging of an image of the light source to infinity arise when the objective element is changed, for example, when a principal objective of an observation device is changed for another objective element with a different focal length. Then the circumstance may arise that the image of the light source is no longer found precisely at the front focal point of the objective element, but rather behind it or in front of it. The spot size on the fundus of an eye varies due to this. However, this does not lead to an increase in the light intensity on the fundus, but only to a reduction of the light intensity, which presents no additional risk to the eye to be observed.

For example, the intermediate image of the light source can lie in the range between 150 mm and 250 mm in front of the objective element, viewed in the direction of the light.

The objective element may have a focal length in the range of 150 to 350 mm, in particular a focal length of 175 mm, or of 200 mm, or of 225 mm, or of 300 mm.

In another embodiment, the objective element can have a variable focal length, preferably by means of moving at least one optical element, so as to cover the range, for example between 150 mm and 550 mm, for example between 150 mm and 300 mm, or between 200 mm and 550 mm, or, of course, another range of focal lengths. Such an objective element, for example, can comprise two groups of lenses disposed one behind the other, in which at least one of the two groups of lenses is driven along the axis of rotational symmetry of this objective element.

In another embodiment, means can be provided in order to superimpose coaxially in each case at least one observation beam bundle and at least one illumination beam bundle. These means can be configured in the most diverse way and can be disposed at the most diverse sites. Several nonexclusive examples will be explained below for this purpose.

For example, it may be provided that the means for superimposing are disposed in such a way that a superimposition of the observation beam bundle and the illumination beam bundle is made above the objective element. The superimposition of the observation beam bundle and the illumination beam bundle can be made, for example, in the parallel beam path over the principal objective.

As has been stated above, the invention is not limited to specific types of embodiment of "superimposition means". For example, the means for superimposing can have at least one optical element in the form of a prism and/or a beam-splitter plate and/or a mirror, e.g., a semi-reflecting mirror and/or a perforated mirror. Of course, the means may also be configured in another way, so that the invention is not limited to the named examples.

In another embodiment, the illumination device can advantageously have at least one optical element for avoiding stray light. This element may involve, for example, a diaphragm, which can be configured as a fixed or variable diaphragm. For example, such a diaphragm can be designed as a discrete diaphragm, as an LCD (liquid crystal display) display, as a DMD (digital mirror device), as an LCOS (liquid crystal on silicon) or as an FLCOS (ferroelectric liquid crystal on silicon). Other transmissive or reflective displays are also conceivable.

Parts of the reflection light that arise are imaged in the eye of an observer by the observation optics unit of the observation device and thus lead to disruptive bright spots in the image. This reflection light is, of course, part of the illumination light utilized and is thus related to it. If the reflection light is then covered by a diaphragm at one site in the illumination optics unit, parts of the illumination light utilized are also stopped down. The calculated localization of this disruptive reflection light shows differences in relation to the useful light for illumination, and in fact is dependent on the site within the illumination optics unit. Depending on the position of the diaphragm, the illumination light is clearly or slightly attenuated.

On the one hand, the light source reflects in a defined angular range. The light that is emitted from the light source diverges. The larger the beam aperture is, the larger is the cross section of the light bundle with increasing distance to the light source or to the image of the light source.

The disruptive reflection light, on the other hand, however, is dependent on the angle at which it strikes the objective element, for example, the principal objective. A limited angular range of the reflection light is included by the observation optics unit of the observation device.

The further away one is from the intermediate image of the light source in the illumination device, the further the disruptive reflection light in the illumination beam cross section migrates away from the illumination axis. This means that the larger angles of the beam apertures produce the disruptive light. The closer the reflection diaphragm is brought to the intermediate image of the light source, then the greater is the actual non-disruptive aperture coverage region.

The optimal arrangement of the diaphragm in the illumination beam path thus represents a particular challenge. Advantageously, it may be provided that the diaphragm is disposed in front of the superimposing means in the illumination beam path. In another embodiment, it may be provided that the diaphragm is disposed in front of the objective element in the illumination beam path.

The optimal site for a reflection diaphragm lies as far removed as possible from the intermediate image of the light source. This may be, for example, in front of the superimposing means, e.g., the splitter plate.

As it was stated above, the invention is not limited to a specific number of light sources or their embodiment. Advantageously, two or more light sources may be provided, each light source producing an illumination beam path or an illumination beam bundle. Thus independent light sources can be used, whereby each light source produces its own partial illumination beam bundle. Or, however, only a single light source can be provided, whereby means are then provided for dividing the illumination beam path or the illumination beam bundle of the light source into two or more illumination beam paths or partial illumination beam bundles. Here, suitable beam splitters in the form of prisms, semi-reflecting mirrors and similar means can be employed.

The present invention is not limited to the use of specific light sources. Several nonexclusive, advantageous examples will be named below for this purpose. For example, the at least one light source can be designed as a lamp, in particular as a halogen lamp or a xenon lamp, as a laser, as a non-thermal radiator, as a light guide, in particular as a bundle of optical fibers, as at least one LED (light-emitting diode), as at least one OLED (organic light-emitting diode), or similar source. Of course, combinations of different light sources are also possible.

In another embodiment, the light source is formed from an arrangement of one or more miniature light source(s) that can be switched on individually or by regions. The illumination device is configured such that it can be varied in a simple manner with respect to the geometry of the luminous field that it produces. In this way, the miniature light sources will be controlled—in particular, electronically—from the outside, preferably by a control device. Another feature provides that the miniature light sources can be controlled, at least in regions, in order to be able to adjust variable illumination geometries. This is particularly of advantage in the case of the generation of annular illumination beam bundles. The invention is thereby not limited to specific sizes and/or shapes of regions. In the simplest case, a single point can be controlled in such a way. Particularly when the luminous source is formed from a matrix comprising individual miniature light sources, one or more miniature light sources can be controlled individually or in groups, whereby in the last-named case, individual miniature light sources can be combined into one region. Also, in this respect, the invention is not limited to concrete embodiments.

For example, the light source can be formed from an arrangement of one or more light-emitting diode(s) (LEDs), in particular organic light-emitting diode(s) (OLEDs). Organic light-emitting diodes were originally developed as microdisplays. Unlike LCDs, which require a backlighting, OLEDs by themselves illuminate as Lambert radiators (surface emitters).

As patterned illumination sources, OLEDs offer a good light efficiency and small structures without intermediate dark spaces. Depending on the desired illumination geometry, individual miniature light sources can be turned on and others can remain turned off. The filling factor is higher in OLEDs as opposed to LEDs, which means that a higher packing density can be provided. The use of a display of LEDs or OLEDs makes possible a programmable switching, and also, for example, an automatable switching of different lighting modes, without having to move mechanical components, such as, e.g., phase contrast rings, filters, reducers and similar components. Particularly suitable, for example, are white OLEDs, whose spectrum is determined by a mixing of organic molecules.

In another embodiment, for the coaxial illumination of two observation beam paths, a common illumination optics unit or two separate illumination optics units can be provided. In particular, for the coaxial illumination of two observation beam paths or observation beam bundles, the illumination beam paths or illumination beam bundles of the collector can be produced, for example, by a common illumination optics unit or two separate illumination optics units. For example, in the case of several illumination beam paths or illumination beam bundles, it can be provided that each illumination beam path or each illumination beam bundle has its own illumination optics unit. In another embodiment, a single, common illumination optics unit can be provided for each illumination beam path or each illumination beam bundle.

The illumination device can be designed preferably as an illumination device in an operating microscope, in particular in an ophthalmologic observation device, preferably in an operating microscope designed for cataract extraction.

According to a second aspect of the invention, an observation device is provided, particularly an operating microscope, having one, two or more observation beam paths, each having at least one observation beam bundle, and with an illumination device having at least one light source for producing at least one illumination beam path with at least one illumination beam bundle for illuminating an object to be observed, in particular, an eye to be observed, additionally having at least one illumination optics unit, which is constructed according to the Köhler principle of illumination, as well as an objective element, wherein the at least one illumination beam path or the at least one illumination beam bundle runs coaxially to an observation beam path or observation beam bundle, in which an intermediate image of the light source lies in the front focal point of the objective element, viewed in the direction of the light, or an intermediate image of the light source lies at a distance from the front focal point of the objective element corresponding to a maximum of 50% of the focal length of the objective element, viewed in the direction of the light.

The objective element of the illumination device may involve, for example, the principal objective of the observation device, so that what has been stated above with respect to the objective element of the illumination device also applies in connection with such a principal objective of the observation device.

For example, the principal objective of the observation device or the objective element of the illumination device can be disposed in an exchangeable manner.

Advantageously, the illumination device is constructed in the way described above, according to the invention, so that reference is made to the full content of the statements corresponding thereto.

The observation device may have, for example, a principal objective element, which is identical to an objective element of the illumination device, whereby means are provided in order to superimpose in each case an observation beam path or an observation beam bundle and an illumination beam path or an illumination beam bundle and whereby the means for superimposing are disposed in such a way that a superimposition of observation beam path or observation beam bundle and illumination beam path or illumination beam bundle is made above the principal objective element.

The observation device can be designed preferably as an operating microscope, in particular as an ophthalmologic observation device, preferably as an operating microscope designed for cataract extraction.

Figure 1:
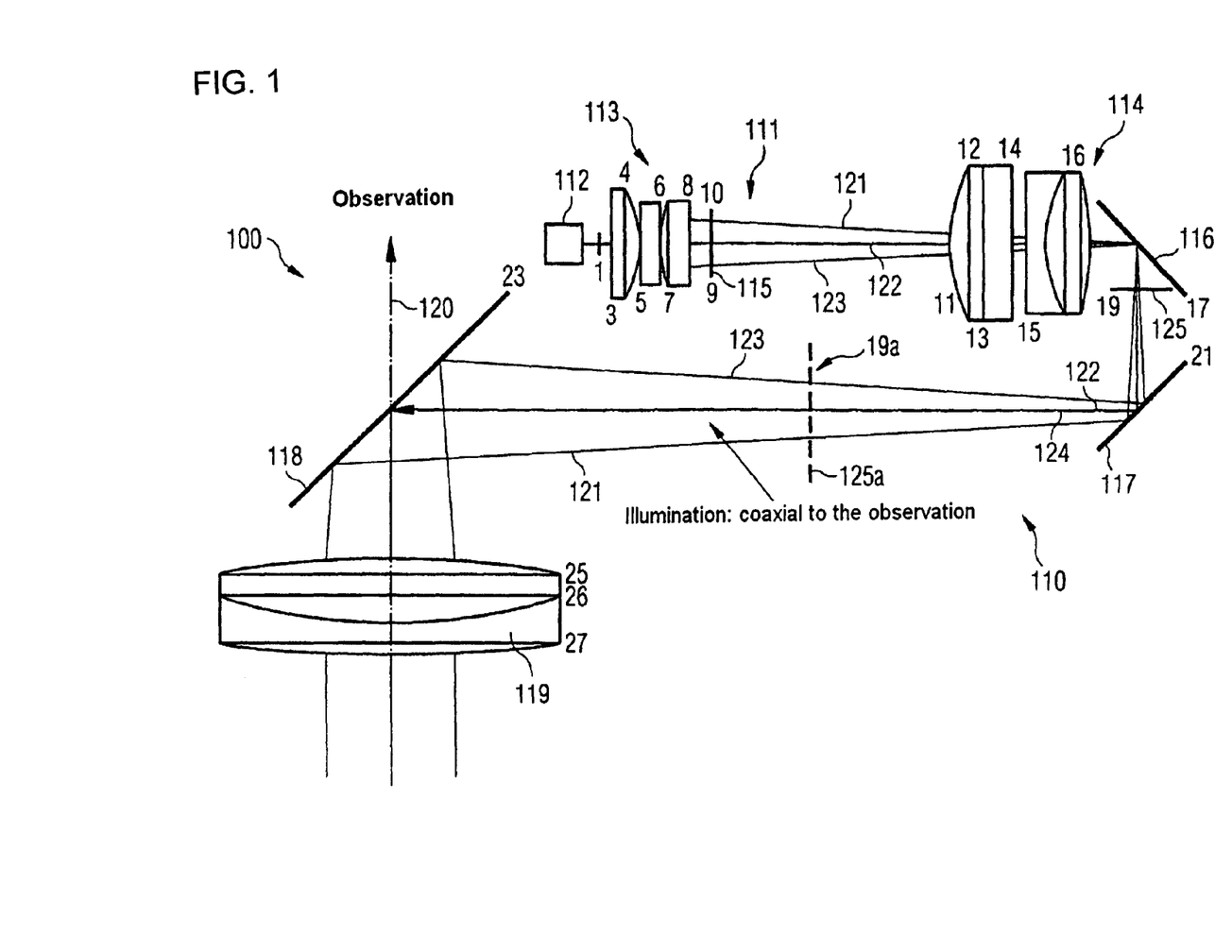
FIG. 1 shows in a schematic view an example of embodiment of an illumination device according to the invention with an illumination optics unit, which is constructed according to the Köhler principle of illumination.

The invention will now be explained in more detail on the basis of embodiment examples with reference to the appended drawings. Here:

FIG. 1 shows an illumination device 110, which can be used in an observation device 100 designed as an operating microscope, in particular as a stereo microscope.

The illumination device 110 has an illumination optics unit 111 that is constructed according to the Köhler principle of illumination. First, a light source 112 is provided, for example, an optical fiber or a bundle of optical fibers. The fiber end of one or more optical fiber(s) is imaged in an intermediate image in an aperture diaphragm (not shown) by a collector 113, which comprises one or more lens elements, each comprising one or more lens members. In addition, a condenser 114 is provided, which in turn may comprise a number of lens elements. Light source 112 of illumination device 110 simultaneously illuminates a luminous field diaphragm 115.

The object to be observed will involve an eye in the present example. Due to the embodiment described above, the cornea of the eye under investigation is illuminated telecentrically, and the eye images light source 112 again on the retina. This light is reflected at the red retina and illuminates uniformly, intensively and in a contrast-rich manner the lens of the patient's eye that is to be operated on, for example.

The light emitted from light source 112 passes through the optical elements of the illumination optics unit and is deflected via deflecting means 116, 117, 118 in the direction of an objective element 119. The objective element 119 simultaneously involves the principal objective of the operating microscope 100.

For simplification, only the observation axis 120 of the observation beam path is shown.

The illumination light, which is shown schematically in FIG. 1 by three illumination beam bundles 121, 122, 123, in which the illumination beam bundle 122 runs along the illumination axis 124, is imaged via the principal objective 119 and coaxially superimposed with the observation beam path or the observation beam bundles.

An example of embodiment is shown in FIG. 1, in which a two-channel illumination is provided above the principal objective element 119 of the operating microscope 100. An illumination optics unit 111 is found in each of the two illumination beam paths, which are formed parallel to one another. The light can be produced by a single light source 112, in which the light is split, but it can also be produced by two separate light sources. Each of the two illumination beam paths, when entering the objective element 119, runs coaxially to a corresponding observation beam path. In another embodiment, it is also conceivable that only a single "large" illumination optics unit is used, which the two illumination beam paths pass through.

Figure 2:
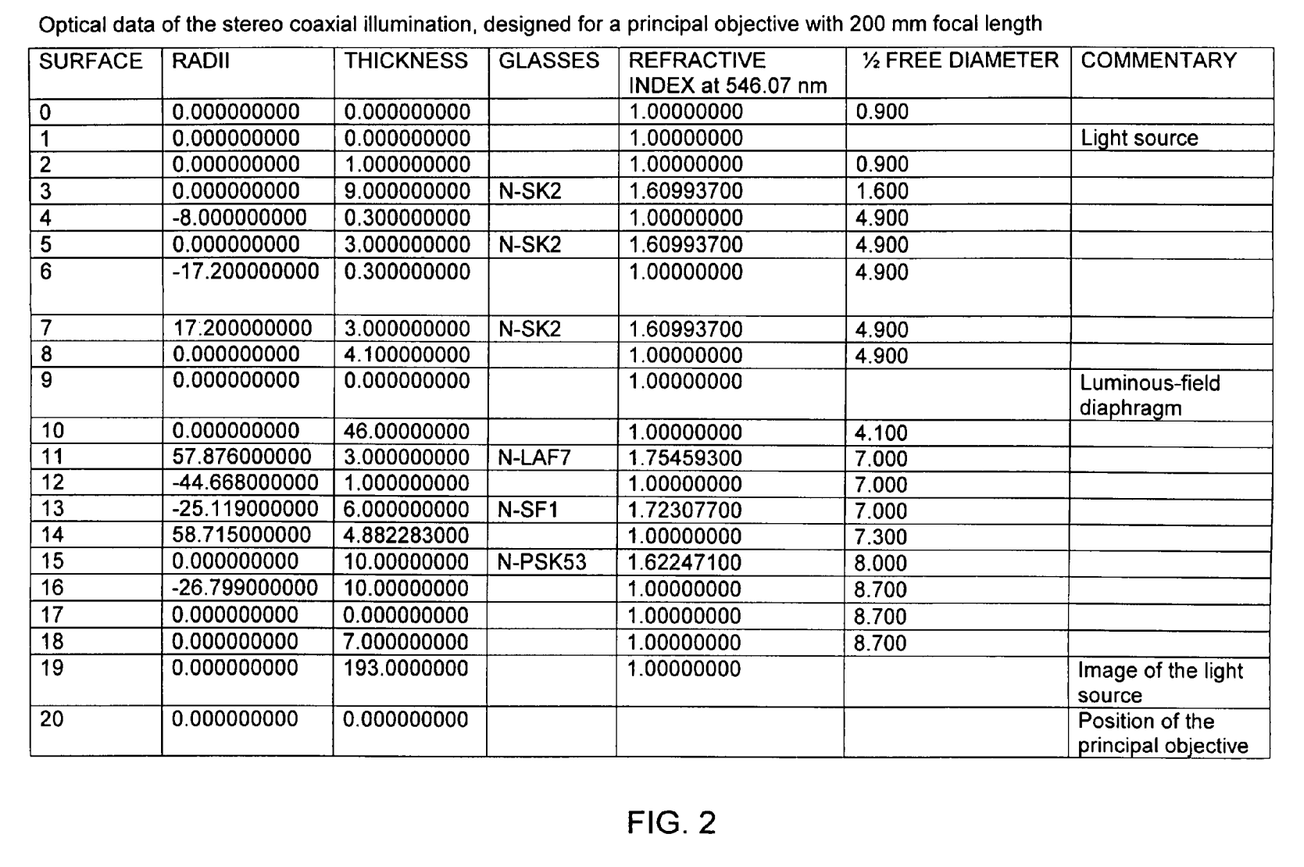
FIG. 2 gives the optical data for the optical elements shown in FIG. 1.

Light source 112 is accordingly imaged to infinity on surface 19, via the principal objective 119, and then accordingly through the eye to be observed onto the fundus thereof. The luminous field diaphragm 115 is imaged by its surface 10 in the back focal point—viewed in the direction of the light—of the principal objective element 119 or in the object plane of the principal objective element, via the subsequent optical elements. The individual data of the different optical elements as well as their surfaces, which are also shown in FIG. 1 and are numbered correspondingly, are compiled in FIG. 2.

In the illumination device 110 according to the invention, the intermediate image 125 of the light source 112, which is characterized by the surface 19, surface 19 only being shown schematically in FIG. 1, is found in the front focal point or in the vicinity of the front focal point of the principal objective element 119—viewed in the direction of the light. An alternative embodiment provides that the intermediate image 125a of light source 112, which is characterized by a surface 19a, which is shown by the dashed line, surface 19a in turn only being shown schematically in FIG. 1, lies in the vicinity of the front focal point of the principal objective element 119, approximately at a distance from the front focal point of the principal objective element 119 corresponding to the maximum 50% of the focal length of the principal objective element 119. Accordingly, in the case of light source 112, surface 19 is only imaged to infinity by the principal objective element 119 characterized by the surfaces 25 to 27. This corresponds to an imaging of light source 112 on the fundus of the eye to be observed. In the example of embodiment, the intermediate image 125 of the light source 112 is found in the front focal point of the principal objective element 119, which has a focal length of f=200 mm. Here, this advantageously involves the nominal focal length of the principal objective element 119 for the layout.

Deviations from the imaging of the intermediate image 125 of light source 112 to infinity can occur when the principal objective element 119 of f=200 mm is exchanged for objective elements with different focal lengths, for example f=175 mm or f=225 mm. The intermediate image 125 of light source 112 according to surface 19 then is no longer found exactly in the front focal point of the principal objective element 119, but is found somewhat in back or in front. The spot size on the fundus varies because of this. Such a variation, however, is tolerable and does not lead to an increase in the light intensity on the fundus, but only to a reduction of the light intensity, whereupon no additional risk arises relative to the eye to be observed.

In order to avoid reflections, in addition, a device (not shown) for avoiding stray light, for example, a diaphragm or similar device, can be provided in the illumination device 110, particularly in the illumination beam bundles 121, 122 and 123.

The intermediate image 125 of light source 112 according to surface 19 advantageously lies between 150 mm and 250 mm in front of the principal objective element 119. In the example of embodiment shown, the intermediate image 125 of the light source 112 according to surface 19 can lie 193 mm in front of the principal objective element 119 in the case of a principal objective element 119 with a focal length of f=200 mm.

The illumination device 110 according to the invention is particularly suitable for principal objective elements 119 with focal lengths between f=150 mm and f=300 mm. A variation of the spot sizes on the fundus of the eye to be observed is harmless when the principal objective element 119 is changed.

Different types of light sources 112, which can be utilized in connection with the illumination device 110 according to the invention are shown in FIGS. 3 to 8.

Figure 3:
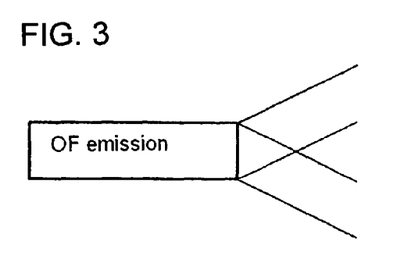
FIGS. 3 to 8 show the light emission behavior of different types of light sources.
Figure 4:
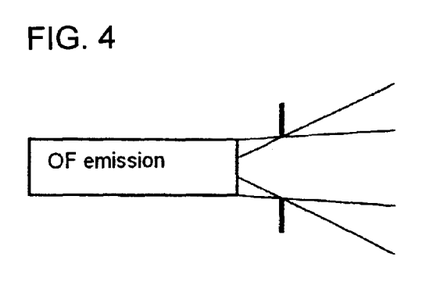
Figure 5:
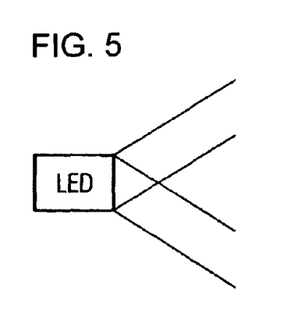
Figure 6:
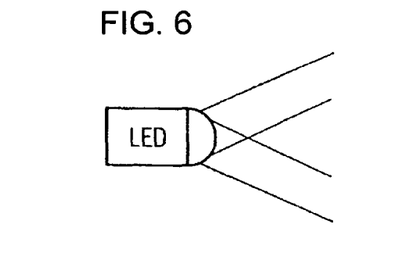
Figure 7:
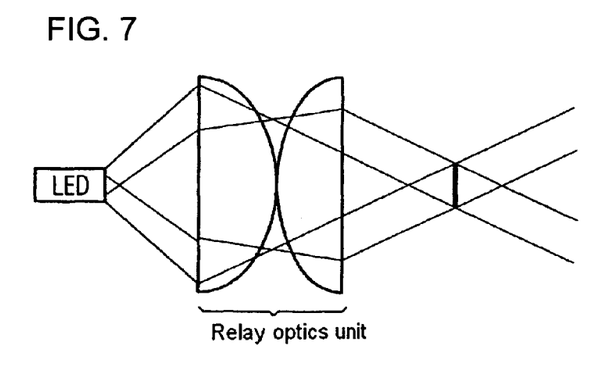
Figure 8:
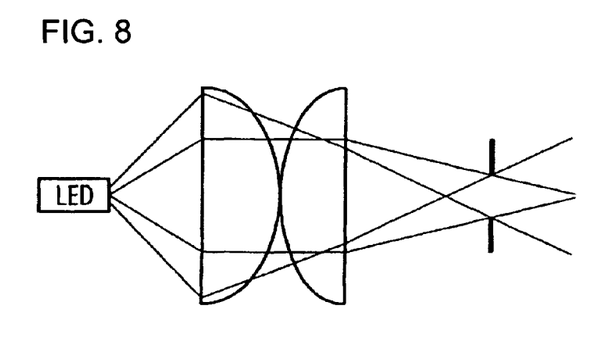

FIG. 3 shows the emission surface of an optical fiber OF with primary light sources, such as, for example, halogen, xenon, LED with optical fiber coupling, and the like. FIG. 4 shows the emission of the optical fiber with a diaphragm connected in front. FIG. 5 shows the emission of a light source that is designed in the form of LEDs, OLEDs, or arrays thereof. FIG. 6 shows the emission of a light source as is shown in FIG. 5, but with a collector lens. FIG. 7 shows the emission of a light source as is shown in FIG. 5, in which an intermediate image is produced by means of a relay optics unit with desired imaging scale factor. FIG. 8 shows an arrangement as shown in FIG. 7, this time with a diaphragm in front of or behind the intermediate image.

List Of Reference Symbols
100 Observation device (operating microscope)
110 Illumination device
111 Illumination optics unit
112 Light source
113 Collector
114 Condenser
115 Luminous-field diaphragm
116 Deflecting means
117 Deflecting means
118 Deflecting means
119 Objective element (principal objective element)
120 Observation axis
121 Illumination beam bundle
122 Illumination beam bundle
123 Illumination beam bundle
124 Illumination axis
125a Intermediate image of the light source

The invention claimed is:

1. An illumination device for an observation device having one, two or more observation beam paths, each with at least one observation beam bundle, in particular for an operating microscope, having at least one light source for producing at least one illumination beam path with at least one illumination beam bundle for illuminating an object to be observed, in particular, an eye to be observed, in addition having at least one illumination optics unit, which is constructed according to the Köhler principle of illumination, as well as an objective element, wherein the at least one illumination beam path or the at least one illumination beam bundle runs coaxially to an observation beam path or observation beam bundle, hereby characterized in that an intermediate image of the light source lies in the front focal point of the objective element, viewed in the direction of the light, or that an intermediate image of the light source lies at a distance from the front focal point of the objective element corresponding to a maximum of 50% of the focal length of the objective element, viewed in the direction of the light.

2. The illumination device according to claim 1, further characterized in that the objective element is also formed as an objective element of an observation device, in particular as its principal objective.

3. The illumination device according to claim 1, further characterized in that the intermediate image of the light source lies at a distance from the front focal point of the objective element corresponding to a maximum of 40% of the focal length of the objective element, viewed in the direction of the light.

4. The illumination device according to claim 1, further characterized in that an intermediate image of the light source lies in the range between 150 mm and 250 mm in front of the objective element, viewed in the direction of the light.

5. The illumination device according to claim 1, further characterized in that the objective element has a focal length in the range of 150 to 350 mm.

6. The illumination device according to claim 1, further characterized in that the objective element has a variable focal length in the range of 150 to 550 mm.

7. The illumination device according to claim 1, further characterized in that means are provided in order to coaxially superimpose at least one observation beam bundle and at least one illumination beam bundle in each case.

8. The illumination device according to claim 1, further characterized in that this device has at least one optical element for avoiding stray light.

9. The illumination device according to claim 1, further characterized in that two or more light source are provided and that an illumination beam path or an illumination beam bundle is produced by means of each light source, or that a single light source is provided and that means are provided for dividing the illumination beam path or the illumination beam bundle of the light source into two or more illumination beam paths or illumination beam bundles.

10. The illumination device according to claim 1, further characterized in that a common illumination optics unit or two separate illumination optics units are provided for the coaxial illumination of two observation beam paths.

11. The illumination device according to claim 3, further characterized in that the intermediate image of the light source lies at a distance from the front focal point of the objective element corresponding to a maximum of 30% of the focal length of the objective element, viewed in the direction of the light.

12. The illumination device according to claim 3, further characterized in that the intermediate image of the light source lies at a distance from the front focal point of the objective element corresponding to a maximum of 20% of the focal length of the objective element, viewed in the direction of the light.

13. An observation device, in particular, an operating microscope, having one, two or more observation beam paths, each with at least one observation beam bundle, and with an illumination device, having at least one light source for producing at least one illumination beam path with at least one illumination beam bundle for illuminating an object to be observed, in particular, an eye to be observed, in addition having at least one illumination optics unit, which is constructed according to the Köhler principle of illumination, as well as an objective element, wherein the at least one illumination beam path or the at least one illumination beam bundle runs coaxially to an observation beam path or observation beam bundle, hereby characterized in that an intermediate image of the light source lies in the front focal point or in the region of the front focal point of the objective element, viewed in the direction of the light, or that an intermediate image of the light source lies at a distance from the front focal point of the objective element corresponding to a maximum of 50% of the focal length of the objective element, viewed in the direction of the light.

14. The observation device according to claim 13, further characterized in that the illumination device is designed such that an intermediate image of the light source lies in the front focal point of the objective element, viewed in the direction of the light, or that an intermediate image of the light source lies at a distance from the front focal point of the objective element corresponding to a maximum of 50% of the focal length of the objective element, viewed in the direction of the light.

15. The observation device according to claim 13, further characterized in that the observation device has a principal objective element, which is identical to an objective element of the illumination device, that means are provided in order to superimpose in each case an observation beam path or an observation beam bundle and an illumination beam path or an illumination beam bundle and that means for superimposing are disposed in such a way that a superimposition of observation beam path or observation beam bundle and illumination beam path or illumination beam bundle is made above the principal objective element.

\* \* \* \* \*

UNITED STATES PATENT AND TRADEMARK OFFICE
CERTIFICATE OF CORRECTION

PATENT NO. : 8,353,596 B2  
APPLICATION NO. : 12/653973  
DATED : January 15, 2013  
INVENTOR(S) : Hoegele Page 1 of 1

It is certified that error appears in the above-identified patent and that said Letters Patent is hereby corrected as shown below:

On the title page item [73], delete "Meditech" should read --Meditec--.

Signed and Sealed this  
Eighth Day of April, 2014

Michelle K. Lee  
*Deputy Director of the United States Patent and Trademark Office*